United States Patent [19]

Borggren

[11] 4,150,297

[45] Apr. 17, 1979

[54] X-RAY EXAMINATION APPARATUS

[75] Inventor: Arne Borggren, Järfälla, Sweden

[73] Assignee: Siemens Aktiengesellschaft, Berlin & Munich, Fed. Rep. of Germany

[21] Appl. No.: 772,317

[22] Filed: Feb. 25, 1977

[30] Foreign Application Priority Data

Mar. 1, 1976 [DE] Fed. Rep. of Germany ....... 2608461

[51] Int. Cl.² ............................................ H01J 35/16
[52] U.S. Cl. ..................................... 250/490; 250/523
[58] Field of Search ........... 250/523, 490, 444, 445 R, 250/446, 447, 448, 449

[56] References Cited

U.S. PATENT DOCUMENTS

| 2,818,510 | 12/1957 | Verse | 250/523 |
| 3,281,598 | 10/1966 | Hollstein | 250/523 |
| 3,617,749 | 11/1971 | Massiot | 250/523 |

Primary Examiner—Craig E. Church
Attorney, Agent, or Firm—Hill, Gross, Simpson, Van Santen, Steadman, Chiara & Simpson

[57] ABSTRACT

An apparatus for exposing selected portions of a patient's body to X-radiation and imaging rays transmitted through the body onto a receiver, such as film, wherein an X-ray source and receiver are mounted on arms offset from opposite ends of a semicircular carrier member supported on a circumference thereof for rotation through at least a full 180° arc in a vertical or tilted plane passing through the body. The centers of the carrier member and support mount are unobstructed and the extension arms are carried on a radially-inside surface of the carrier member to avoid interference between the parts during rotation through the arc. Three sets of bearings which are spaced-apart along a guide track in the support mount support the carrier member radially and axially with at least two of the bearings engaged with the carrier member even at extremes of rotation thereof.

5 Claims, 2 Drawing Figures

X-RAY EXAMINATION APPARATUS

BACKGROUND OF THE INVENTION

1. Field of the Invention

The present invention relates to an X-ray examination apparatus which is tiltable and pivotable about perpendicular axes passing through a body or object being examined.

2. The Prior Art

Devices for selectively adjusting the position of X-ray sources and image receivers with respect to the body of a patient remaining in a fixed position have become recognized as having substantial advantages over devices wherein the patient was moved with respect to fixed X-ray apparatus. The newer devices are particularly useful in surgical situations and in new body scanning applications wherein transverse sections of the body may be examined with computer analysis of multiple X-ray transmissions through the section.

An X-ray examination apparatus is known in which an X-ray tube and an X-ray image intensifier are mounted on opposite ends of a carrier member having a semicircular bend or arcuate curvature. The carrier is supported in a support mounting to be movable or displaceable along its circumference in a vertical plane and is also pivotally mounted for tilting its plane about a horizontal axis lying in the plane of the carrier and passing through the center of the semicircle. In this apparatus, the central ray of the X-ray tube always passes through the center of the semicircle regardless of tilting of the carrier plane or displacement of the carrier along its circumference in the support mounting. Simultaneous examination of a patient on a table using two such X-ray apparatuses in two different planes of the body is, however, usually impossible because of interference between the two sets of apparatus. In addition, adjustment of the X-ray tube and receiver is restricted by the mounting of the parts directly on the curved carrier. For example, adjustment of the X-ray tube by pushing the carrier in the direction of its curvature is not possible, but rather the entire carrier must be moved.

Other apparatus is known having a semicircular carrier with an X-ray tube and an image receiver mounted on extension arms fixed thereto and extending from one side of the plane of the carrier. Such apparatus permits positioning of two such devices so that the central rays of the two devices intersect at a right angle without interference between the sets of apparatus. In such devices, however, the adjustment range of the radiation source and image receiver is restricted to approximately 45° in each direction from a vertical, middle position because the center of the carrier is not open but rather is obstructed by the supporting parts. Such prior apparatus cannot be used in a horizontal position without further swiveling of the holder itself.

Thus, it is desirable to provide an X-ray examination apparatus having an enlarged adjustment range.

SUMMARY OF THE INVENTION

An X-ray examination apparatus comprises a support mounting having an arcuately-curved guide track. A carrier member is arcuately curved in a plane and about an axis transverse to the plane and has a side engaged in the guide track for relative movement therealong. The carrier member further has arcuately-opposite first and second ends spaced by at least 180° along said member and an exposed inner circumferential surface. First and second extension arms are fixed adjacent corresponding ones of said ends of said carrier member at substantially a 180° spacing therealong. The arms extend transversely from the member on one side of a plane thereof. A radiation source is mounted on the first extension arm for producing X-radiation and directing same selectively radially inwardly on said carrier member and parallel to the plane thereof. An image receiver, such as a film unit or an image intensifier unit, is mounted on the second extension arm for receiving X-radiation from the radiation source after transmission through the body of a patient being examined. The support mounting and guide track do not extend radially inwardly of the inner surface of the carrier member, so that the carrier member may be swiveled in the support mounting in its plane along the guide track through substantially at least 180° without interference between the extension arms and the support mounting. The support mounting further includes rotation apparatus for rotating the guide track and the carrier member therein about an axis in a plane parallel to the plane of the carrier member and intersecting the radiation source and the image receiver.

THE DRAWINGS

THE PREFERRED EMBODIMENTS

Figure 2:
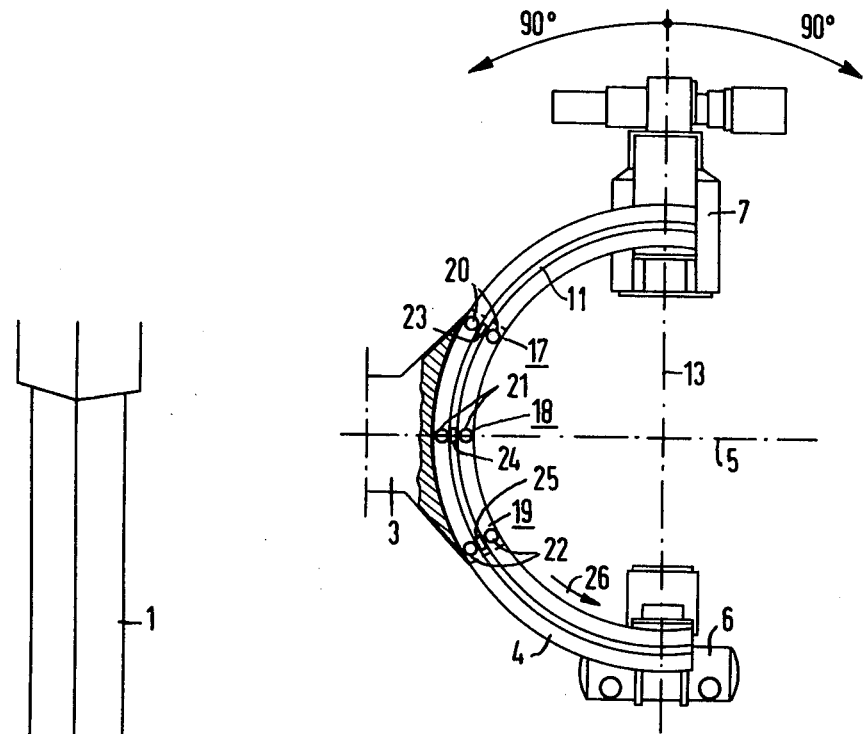
FIG. 2 is a front plan view of a portion of the apparatus, partly cut away.
Figure 1:
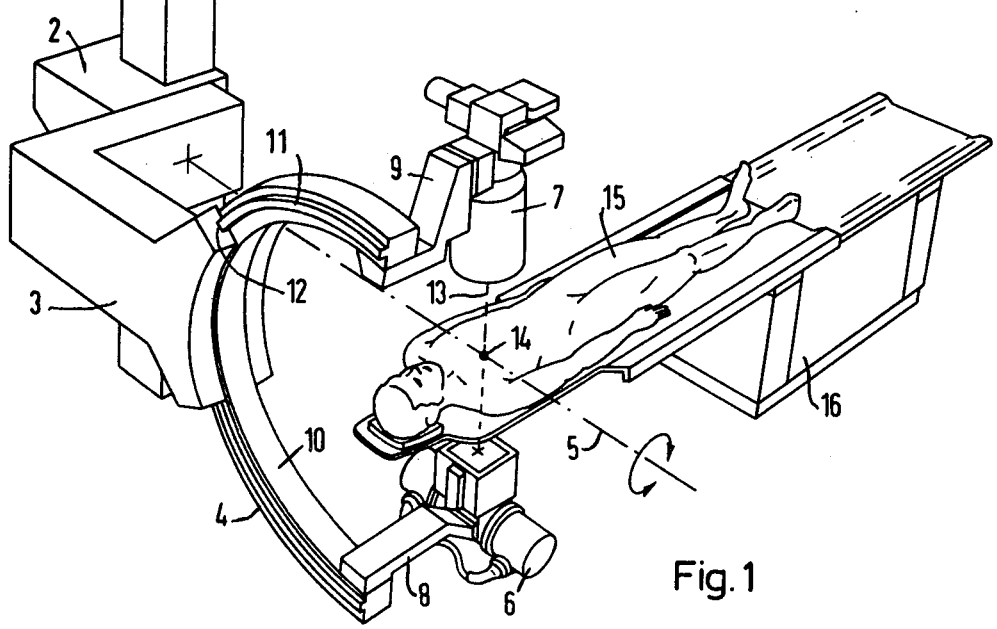
FIG. 1 is a general perspective view of the apparatus of the present invention.

A support column or pillar 1 in an X-ray examination room carries a support carriage 2 thereon for vertical adjustment. As shown in FIG. 1, a support mounting 3 is carried on the support carriage 2, to support a carrier member 4. The support member 3 is rotatably adjustable about a horizontal axis 5 by means of apparatus carried within the support carriage 2. The carrier member 4 is arcuately curved through a semicircle of at least 180° and is supported in the support mounting 3 for pivoting or tilting about the axis 5.

Spaced 180° apart about the carrier 4 is an X-ray tube 6 and an X-ray receiver and image intensifier 7. These parts are supported on respective first and second extension arms 8, 9. The arms 8, 9 extend from the plane of the carrier 4 in the same direction and are fixed to a radially inward surface 10 of the carrier member 4 across an entire width thereof in the axial direction.

The carrier member 4 is formed with an axially extending rail 11 on each side surface thereof in the axial direction. The support mounting 3 is formed with a cooperative guide track 12 for aligning and retaining the rail 11 and carrier 4 with the support mounting 3. Other configurations, including use of an I-beam rail on one side only of the carrier 4, are also feasible.

The X-ray tube 6 is aligned with a central ray 13 thereof directed to the center of the receiver unit 7. The central ray 13 and the horizontal axis 5, about which the support mounting 3 and the carrier 4 are rotatable, define a 90° angle with one another. The arms 8 and 9 maintain the X-ray tube 6 and the image-receiving unit 7 at a distance from the plane of the curved carrier 4 so that the central ray 13 of the X-ray tube 6 always intersects the horizontal axis 5 at the same reference point 14. The carrier 4, which is substantially rectangular in cross-section, includes rails 11 raised from opposite lateral sides thereof. The rails 11 are received in a guidance groove means 12 in the support mounting 3 as shown. In the vicinity of the groove means 12, the support mounting 3 is provided with a plurality of roller bearing means for ease of movement and guidance of the carrier 4 relative to the support 3, as will be described later.

The supporting mounting 3 is unobstructed through the center of the carrier 4 and leaves the inside surface 10 of the carrier 4 free over its entire length. Because of this arrangement, the extension arms 8, 9 may be moved into positions adjacent the vertical center of the support mounting 3 and into a horizontal alignment with one another in either direction from the vertical. Thus, the central ray 13 of the tube 6 may be aligned or directed onto the patient 15 lying on an extension of the examining table 16 in both horizontal and vertical positions without having to swing the support mounting 3 about its axis 5.

Further in accordance with the invention, at least three sets of roller bearings 17, 18 and 19 are rotatably supported in the support mounting 3 adjacent the guide track 12 thereof. Each set of roller bearings 17-19 comprises three pairs of bearings 20, 21, and 22 rotatable on axes transverse to the plane of the carrier 4 for supporting the carrier in a radial direction via the rail 11. Three bearings 23, 24 and 25 rotatable on axes radial to the carrier 4 on each side thereof support and guide the carrier axially. This arrangement of bearings 17-19 insures that the carrier 4 is always supported by at least two of the three sets of bearings 17-19 regardless of the position of the carrier 4 along its circumference. That is, when carrier 4 is swung in the direction of the arrow 26 until the X-ray tube 6 sends its central ray 13 in a horizontal direction, the carrier 4 is supported radially by the bearings 18 and 19. Swinging the carrier 4 in the opposite direction to a horizontal position of the central ray 13 leaves the carrier 4 supported by the central and upper bearings 18, 17.

In the embodiment shown, the carrier has a total arcuate length of approximately 200°. Use of a carrier longer than 200° will permit a range of traverse about the horizontal at either extreme thereof.

Although various minor modifications may be suggested by those versed in the art, it should be understood that I wish to embody within the scope of the patent warranted hereon all such modifications as reasonably and properly come within the scope of my contribution to the art.

I claim as my invention:

1. An X-ray examination apparatus comprising:
   a support mounting have an arcuately-curved guide track;
   a carrier member arcuately curved in a plane and about an axis and having a side engaged in said guide track for relative movement therealong, said carrier member having arcuately-opposite first and second ends spaced by at least 180° along said member, said carrier member having an inner circumferential surface;
   a first and a second extension arm, each fixed adjacent corresponding one of said ends of said carrier member centered at a 180° spacing therealong and extending therefrom transversely to and on one side of a plane of said carrier member;
   a radiation source means mounted on said first extension arm for producing X-radiation and directing said radiation selectively radially inwardly of said carrier member and parallel thereto; and
   an image receiver means mounted on said second extension arm for receiving said X-radiation from said radiation source means;
   said support mounting and said guidetrack extending away from said inner circumferential surface of said carrier member, said support mounting including rotation means for rotating said guide track and carrier member about an axis in a plane parallel to the plane of said carrier member and intersecting said radiation source means and said image receiving means;
   whereby said carrier member may be swiveled in said support mounting in its plane along said guide track through substantially at least 180° without interference between said extension arms and said support mounting.

2. An apparatus as defined in claim 1, wherein the carrier member has a substantially rectangular cross section and wherein the extension arms are engaged with the carrier member over substantially an entire width of the inner circumferential surface thereof parallel to a central axis of said carrier member.

3. An apparatus as defined in claim 2, wherein said guide track comprises a pair of guidance groove means and two sides of said carrier member parallel to said guide track have rails raised therefrom and received in said guide groove means of said guide track.

4. An apparatus as defined in claim 3, wherein said guide track further comprises three pairs of first bearings supporting each of said rails parallel to the plane of the carrier member at locations spaced apart along said guide track and carrier member and three pairs of second bearings supporting each of said rails at said locations transversely to the plane of the carrier member.

5. An apparatus as defined in claim 4, wherein a center one of each of said first and second bearings is positioned to engage said rail in all translational positions of said carrier member together with at least one of the other ones of said bearings.

* * * * *